US010888263B2

(12) United States Patent
Thomas et al.

(10) Patent No.: US 10,888,263 B2
(45) Date of Patent: Jan. 12, 2021

(54) PROCEDURE OF NON-INVASIVE VIDEO-OCULOGRAPHIC MEASUREMENT OF EYE MOVEMENTS AS A DIAGNOSTIC TOOL FOR (EARLY) DETECTION OF NEUROPSYCHIATRIC DISEASES

(71) Applicant: THOMAS RECORDING GMBH, Giessen (DE)

(72) Inventors: Uwe Thomas, Marburg (DE); Stefan Dowiasch, Lohra (DE)

(73) Assignee: THOMAS RECORDING GMBH, Geissen (DE)

( * ) Notice: Subject to any disclaimer, the term of this patent is extended or adjusted under 35 U.S.C. 154(b) by 155 days.

(21) Appl. No.: 16/207,353

(22) Filed: Dec. 3, 2018

(65) Prior Publication Data

US 2019/0246969 A1 Aug. 15, 2019

(30) Foreign Application Priority Data

Feb. 14, 2018 (DE) .................. 10 2018 103 334

(51) Int. Cl.
*A61B 5/16* (2006.01)
*A61B 3/113* (2006.01)
*A61B 3/00* (2006.01)
*A61B 3/14* (2006.01)
*A61B 3/11* (2006.01)
*G06K 9/00* (2006.01)
(Continued)

(52) U.S. Cl.
CPC ............ *A61B 5/163* (2017.08); *A61B 3/0025* (2013.01); *A61B 3/0041* (2013.01); *A61B 3/0091* (2013.01); *A61B 3/112* (2013.01); *A61B 3/113* (2013.01); *A61B 3/145* (2013.01); *A61B 5/7264* (2013.01); *G06K 9/0061* (2013.01); *G06K 9/00281* (2013.01); *G06K 9/00604* (2013.01); *G06T 7/60* (2013.01); *G06T 2207/10016* (2013.01); *G06T 2207/20084* (2013.01); *G06T 2207/30041* (2013.01)

(58) Field of Classification Search
CPC ....... A61B 3/113; A61B 3/0025; A61B 5/163; A61B 3/0041
See application file for complete search history.

(56) References Cited

U.S. PATENT DOCUMENTS

2015/0223683 A1* 8/2015 Davidovics ........ G02B 27/0093
351/210
2015/0305686 A1* 10/2015 Coleman .............. A61B 5/7264
600/301

(Continued)

*Primary Examiner* — John J Lee
(74) *Attorney, Agent, or Firm* — Ronald S. Lombard

(57) ABSTRACT

A method for non-invasive video oculographic measurement of eye movements as diagnostic support for (early) detection of neuropsychiatric diseases, using an indicator for a visual stimulus and a camera for video recording. A position of the camera is kept constant in relation to the display and a face of a test person is continuously recorded, at least in parts. A recognition algorithm is started which creates an eye template in which an absolute position of the eye and a pupil of the eye are continuously recorded in the image. Furthermore, a reference range, especially around the eye, is defined and, after selecting a predefined measurement paradigm of the pupil are continuously recorded and analyzed at the end of the stimulus.

14 Claims, 1 Drawing Sheet

(51) Int. Cl.
*A61B 5/00* (2006.01)
*G06T 7/60* (2017.01)

(56) References Cited

U.S. PATENT DOCUMENTS

2017/0150907 A1* 6/2017 Duffy .................... A61B 5/411
2019/0209070 A1* 7/2019 Cherchi ............... A61B 5/4082

* cited by examiner

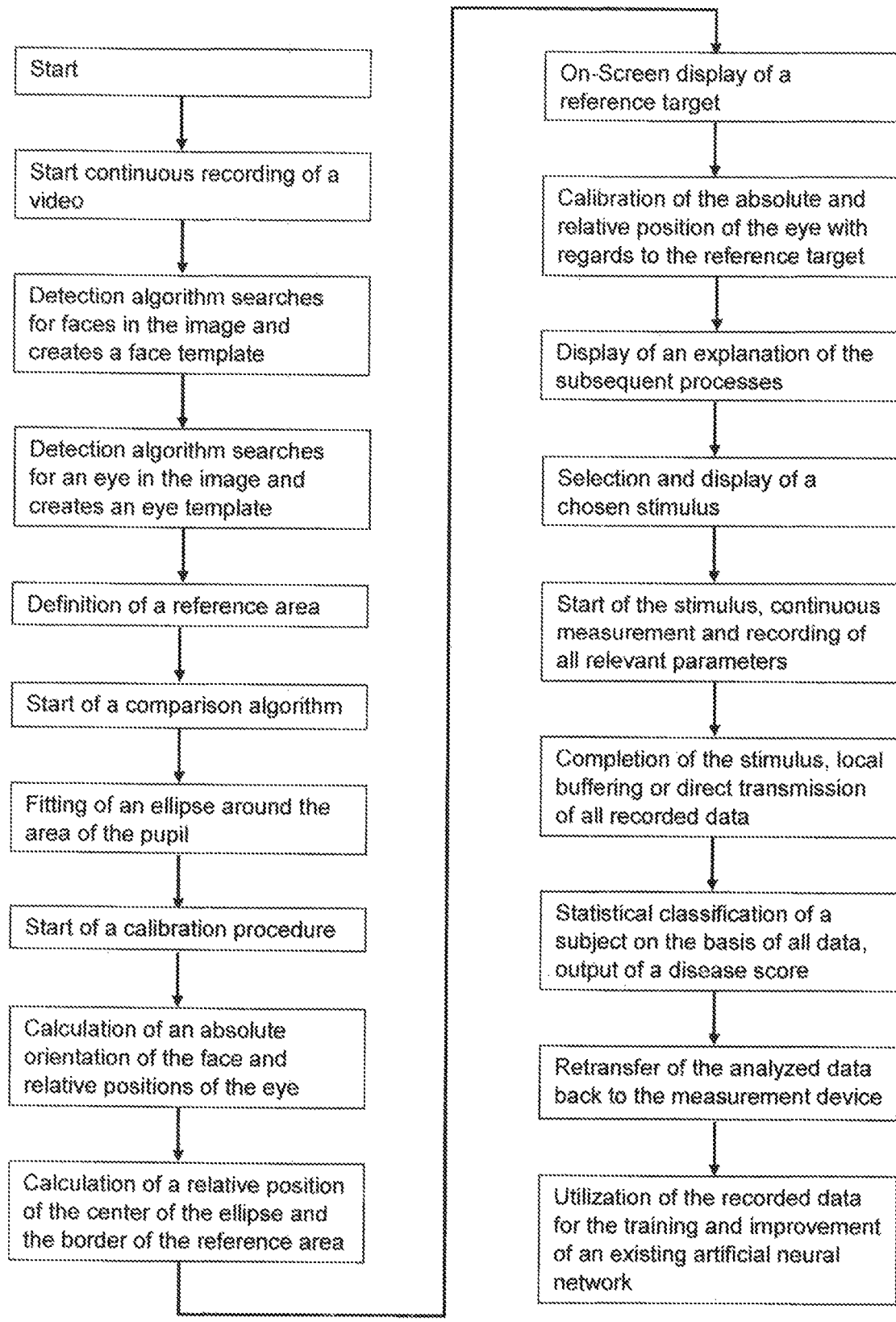

PROCEDURE OF NON-INVASIVE VIDEO-OCULOGRAPHIC MEASUREMENT OF EYE MOVEMENTS AS A DIAGNOSTIC TOOL FOR (EARLY) DETECTION OF NEUROPSYCHIATRIC DISEASES

CROSS-REFERENCE TO RELATED APPLICATION

This is application claims the priority of German Application No. 10 2018 103 334.6 filed Feb. 14, 2018.

BACKGROUND OF THE INVENTION

The invention concerns a method for non-invasive video-oculographic measurement of eye movements as a diagnostic tool for (early) detection of neuropsychiatric diseases, using a display for a visual stimulus and a camera for video recording.

Neuropsychiatric diseases and neurodegenerative diseases such as Parkinson's disease or dementia are common diseases, especially in older people. However, the symptoms of such diseases can differ substantially between subjects and there is a huge overlap with other neurological diseases, which often leads to misdiagnosis, especially in the first years of the disease. Therefore, it is essential for a successful therapy to diagnose the respective disease correctly at an early stage and to differentiate it from related diseases with a correct differential diagnosis. However, conventional clinical neurological examinations are essentially based on an evaluation of symptoms or costly imaging techniques, such as, functional magnetic resonance imaging or positron emission tomography (fMRI, PET). Yet again, these methods can only produce clear diagnostic results in comparatively late phases of the diseases. In addition, both approaches require an interpretation of the data collected by experienced specialists.

It is known that eye movements show characteristic abnormalities in a large number of neurological and psychiatric diseases, which can be used as biomarkers and furthermore derive the presence, stage and often also the type of the disease. As such, eye movement measurement provides an objective and easily accessible parameter of body motor function. Theoretically, this approach allows an early detection of neuropsychiatric diseases even before the onset of the cardinal symptoms.

The examination involves stimulation, ideally tailored to a particular disease, with simultaneous monitoring of eye movement, from which the existence of a neuropsychiatric disease can be deduced. As a stimulus, usually visual stimuli are used that elicit e.g. saccades, anti-saccades, or changes in pupil diameter as a response.

Saccades are fast, ballistic movements of the eyes, which can occur consciously or unconsciously in different directions. They are an active part of perception and serve to bring a stimulus into the area of the fovea on the retina, for example when recording visual stimuli during a search task, during conscious information acquisition or during orientation in the surroundings. Saccades reach angular speeds of up to 1000 degrees/s, have amplitudes of up to 60 degrees and usually last between 30 and 100 ms.

For the eye movement measurement, a fixation target is displayed on a display repeatedly followed by a second target. In the saccade test, this second target has to be focused, while in the anti-saccade test, the goal is to look in the opposite direction, i.e. away from the second target stimulus, or explicitly at a position corresponding to the location of the second target stimulus mirrored at the vertical meridian. In addition, the diameter of the pupil can be analyzed in response to a change in luminance of a stimulus or as a measure of cognitive processes during a test.

Especially in the anti-saccade test, reflexive and voluntary eye movements and their interaction are examined. Because numerous and sometimes different brain regions are involved in controlling these eye movements, conclusions can be drawn about the presence of a neuropsychiatric disease on the basis of these examinations and especially the analysis of the correct and incorrect directions of movement as well as the time required for the execution or correction of the movement.

In order to perform such an examination, usually a relatively complex, stationary apparatus in a special darkened room is required, which, in addition to a high-performance camera with infrared illumination, also requires an opportunity to fixate the patient's head. Furthermore, a detailed training of the operating personnel and the compliance of the patient over a relatively long period of time is necessary in order to achieve diagnostically conclusive results. Finally, as of yet, all existing eye tracking devices are only applicable for basic research and not officially approved as a medical device for the regular treatment of patients.

The invention is now based on the need for a method that enables non-invasive video oculographic measurement of eye movements with little effort. The new procedure should lead to a reliable result as quickly as possible, which can then support the diagnosis of neuropsychiatric diseases.

SUMMARY OF THE INVENTION

This task is solved by a procedure with the features and advantages of the claims.

A method for non-invasive video-oculographic measurement of eye movements of human subjects as diagnostic support for (early) detection of neuropsychiatric diseases is disclosed, wherein a display for a visual stimulus and a camera for video recording images are used, whereby a position of the camera is kept constant with respect to the display and a face of a subject is continuously recorded at least in parts, is inventively designed such that a recognition algorithm is started, which creates an eye template in which an absolute position of the eye and the pupil in the image are continuously recorded, whereby a reference area being in particular around the eye and a position of the pupil and other parameters of the pupil being continuously recorded and analyzed after selection of a predefined measuring paradigm as a stimulus.

With the help of the recognition algorithm, the eye is automatically identified and, with the help of the previously created template continuously tracked during the recording despite any movements. Thus, the absolute position of the eye and the pupil in the image of the camera is continuously recorded throughout the stimulus and can be considered in relation to the position of the reference area. The reference area is placed around the eye and detected, extracted and analyzed using an object recognition algorithm. Since not only the position of the eye, but also that of the reference area, which is fixed relative to the eye, are recorded, head movements that lead to a translatory movement of the reference range and the eye can be included in the calculation of the viewing position from the relative position of the pupil. Therefore, a fixation of the head of the subject is no longer absolutely necessary for reliable eye movement measurements and in particular for determining the absolute gaze direction. Furthermore, the amount of data to be processed is kept to a minimum by focusing on the identified eye and the reference area. As a result of this feasibility of eye movement analysis, a non-invasive, reliable, fast and easily accessible procedure is provided, which can be used to measure dysfunctions in the brain, from which neuropsychiatric diseases can be detected at an early stage of the disease, even before the occurrence of cardinal symptoms.

In a preferred design, coordinates of further characteristic facial features are determined and continuously recorded in a facial template using an object recognition algorithm in cases where a face is detected by the algorithm. In addition to the absolute position of the eye and the pupil, the relative position of the pupil to distinctive points of the face such as the tip of the nose, a corner of the mouth, etc. can thus be determined. By using these distinctive points, the orientation of the face relative to the camera can be easily recorded. This allows for a reliable measurement of a subject's gaze direction while head rotation takes place.

Preferably, the recognition algorithm is terminated after creation of the eye template and/or the face template and a comparison algorithm is started, whereby the position of the reference area in the coordinate system of the camera is continuously detected and recorded. This reduces the required computing power and the amount of data during recording which offers the possibility to also use less powerful components.

Advantageously, the shape of the pupil is nourished by an ellipse, whereby at least one size dimension of the ellipse is detected as a parameter of the pupil and in particular a relative position of a center of the pupil relative to the reference range is determined. Due to the strong difference in reflection or brightness between iris and pupil, the pupil can be easily extracted from the captured image and changes in the pupil can be clearly detected. It is advantageous if a threshold value for the pupil recognition of the camera is adjusted automatically or manually in order to define the transition between iris and pupil as clearly as possible. Common parameters such as the position of a center of the pupil, a length of the two axes and the area of the pupil as well as the viewing direction and the like are determined or derived from this. In high-resolution systems, a torsion of the iris may also be detected and taken into account in the evaluation.

Preferably, a calibration process is started after creating the face template, in which an alignment of the face of a subject to a defined reference target is determined via the face characteristics. This defines a zero direction of the viewing direction and the reference range. The direction of view of the subject is then calculated for each video frame when the position of the eye relative to the patient's head changes compared to the reference range.

It is preferred that after the calibration process at least one visual stimulus in particular is selected from predefined, standardized and validated paradigms and started, whereby in particular a reaction, a response latency, a calculated gaze position, a pupil size and/or a change in pupil position in response to certain stimuli are continuously simultaneously detected and recorded. Predefined stimuli can be provided that are tailored to a particular neuropsychiatric disease and that generate specially validated stimuli parameter combinations. During the examination, a distinction is then made between the desired and undesired reaction to the stimulus, whereby the latter can once again be differentiated into no reaction and incorrect reaction. In addition, all parameters are defined as "normal" or "abnormal" on the basis of a normal range defined individually for each clinical picture. Validated biomarkers that can be used for diagnosis can thus be made available fully automatically.

Preferably, the pupil can be detected and monitored in ambient light. The technical equipment required to carry out the process is thus kept to a minimum and is also possible in environments that are not specially prepared.

In a preferred training course, an additional modular lighting unit is activated in unfavorable lighting conditions. Good results can be achieved even under unfavorable lighting conditions. Various light sources can be considered as additional lighting units, for example also in the infrared range. But even a diffuse lamp working in the visible range can sufficiently improve the measurement results, for example in the dark.

A special advantage is the immediate evaluation of the collected parameters using at least one stored dataset, whereby a result of the evaluation is displayed on the display. After completion of the stimulus, the subject or a physician can thus receive a result after a short time, especially after a few minutes, which can be used for diagnosis. This is a significantly shorter time span, particularly with regard to the time to obtain blood test results, which often exceed 24 hours. It may be provided that the subject only has access to a simplified evaluation, e.g. with display of the determined parameters and the normal ranges, while some physician or other specialist personnel is also provided with extended evaluations, such as calculated and processed diagnostic supports and/or weighted combinations of individual parameters, which allow a probability estimation for the respective tested disease.

Preferably, a classification of the determined parameters is carried out in particular by means of an externally provided artificial neural network, whereby in particular all newly determined parameters are entered and considered in particular for future classifications. This means that a very large amount of data can be accessed, which means that a high correction classification rate can be maintained, which automatically increases further with increasing use of the process. Thus, on the basis of the collected parameters, a statement can be made as to whether and with what probability the subject belongs to the respective disease group belonging to the stimulus or which co-morbidities could still be considered.

The procedure can be conducted in a stationary institution that has a camera or rather a high definition camera as well as a display. An infrared light can be used if needed. Also, a support for the head of the subject can be used to minimize unwanted head movements. Thus, very accurate eye movement measures are possible with high spatial and temporal resolution.

Alternatively, the procedure can be proceeded by using a Tablet-PCs or a smartphone. The availability is facilitated hereby and the eye movement measurement can be conducted at home or in the waiting room of a medical practice.

BRIEF DESCRIPTION OF THE DRAWING

Further features, details and advantages of this invention are the result of the wording of the claims as well as of the following description of execution examples by means of the drawing. It shows:

The single FIGURE is a schematic proceeding of the invention-related process.

DETAILED DESCRIPTION OF THE INVENTION

Individual steps of the procedure are exemplarily portrayed in the single FIGURE. After the start, in which a desired measurement paradigm has already been selected by a medical staff and subject-specific information such as name, age etc. has been entered, a continuous recording of a video begins.

With the help of a recognition algorithm it is tried to detect the recorded face of the subject in the video. If this succeeds a face-template with coordinates of the typical face characteristics will be set up with for example coordinates of reference points as nasal tip, eye or similar.

Regardless of whether a face has been recognized or not, a recognition algorithm is then used to search for an eye and create an eye template in which, for example, geometric dimensions and coordinates are stored. Then a reference range or area is defined using, for example, the coordinates of the left eye and the reference range is selected to completely cover the eye. The position and dimensions of the reference range within the captured image are also saved.

After a successful setting of the eye-template a relatively slow recognition algorithm ends and a comparison algorithm is started. Hereby a faster following of the eye is given if a position change happens, whereby a absolute position of the eye within the coordinate system of the camera is being recorded.

For example, the form of a pupil is approximated by an ellipse through a threshold observation. It is taken advantage of that hereby the reflections and lighting differences between the dark pupil and the iris of the eye are extremely strong. Afterwards a centrum, a horizontal diameter as well as the surface of the ellipse are constantly recorded.

The next step is a calibration process that is triggered manually by the person being examined. If a face template has been created, an alignment of the face is calculated using the face characteristics stored in the face template. For reliable measurement of the viewing direction without fixing the head of the subject, the absolute orientation of the face and simultaneously the relative position of the eye to the orientation of the face are recorded.

In addition, a relative position of a center of the ellipse placed around the pupil in relation to an edge of the reference range, for example the left edge of the reference range in the left eye. A relative position of the pupil in relation to the reference range is monitored, resulting in better independence from small head movements than monitoring the absolute position of the eye. Nevertheless, results are improvable through the stabilization of the head for example through a chin rest.

Subsequently a reference target is shown in the center of the display and the absolute as well as the relative position of the reference target of the fixed eye/pupil as well as the orientation of the face is recorded. The person being examined has to approve the fixation in particular manually and thus finalizes the calibration.

The procedure is now ready to start the single eye movement measurement for a selected stimulus. If necessary, an explanation of the further process can be provided and the selected stimulus can be displayed. It is also possible to select the stimulus at this point or to change it again.

The desired stimulus then takes place, for example in the form of several consecutive horizontal prosaccades and antisaccade tasks, which are displayed in pseudo-randomized order. In contrast to anti-saccades, prosaccades are characterized, for example, by a different colored fixation target.

A continuous recording is made with recording of pupil parameters such as size and direction of vision as well as latency and correctness of the executed eye movement.

When the measurement is complete, a corresponding message is displayed. The determined data can either be stored locally, evaluated locally or transmitted to a central server for evaluation. In this evaluation, a statistical classification is made on the basis of all data or parameters determined, whereby a result of this evaluation can then again be displayed on the display. The result can be displayed in detail or more generally, for example in the form of a disease score.

When using a central server and evaluation using artificial neural networks, it is advantageous if the collected parameters and data are used in anonymous form to improve the artificial neural network and in particular to adjust weighting factors. With an increasing number of tests carried out, an improved reliability of the process in the form of a higher correction classification rate can be achieved.

The process can be carried out on a tablet PC, for example, thus enabling variable spatial use without expensive special equipment, using the display and camera already present in the tablet PC. However, the same procedure can also be used in conjunction with permanently installed high-performance cameras and a display, whereby the parameters can usually be recorded with a higher spatial and temporal resolution, whereby more precise results can be achieved.

The invention is not limited to one of the prescribed designs but can be modified in many ways. In particular, the method can be used for diagnostic support or even early detection by selecting appropriate stimuli and eye movement parameters for various neuropsychiatric diseases as soon as a sufficient amount of comparative data is available. This results in a very universal applicability.

All features and advantages resulting from the claims, the description and the drawing, including design details, spatial arrangements and procedural steps, may be essential to the invention, both individually and in a wide variety of combinations.

What is claimed is:

1. A method for non-invasive video oculographic measurement of eye movements as diagnostic support for enhanced detection of neuropsychiatric diseases, wherein a display for a visual stimulus and a camera for video recording are used, wherein a position of the camera is kept constant with respect to the display and a face of a subject is continuously recorded by the camera at least in parts, wherein an object recognition algorithm is started which creates an eye template in which an absolute position of an eye of the subject and a pupil of the eye in an image are continuously recorded by the camera, wherein a reference area, in particular around the eye, is defined and, after selection of a predefined measurement paradigm as visual stimulus, a position of the pupil and parameters of the pupil are continuously recorded by the camera and analyzed upon expiry of the visual stimulus.

2. The method according to claim 1, characterized in that in a case in which the face of the subject is recognized, coordinates of further characteristic facial features are continuously recorded in a face template using the object recognition algorithm.

3. The method according to claim 2, characterized in that an area around the eye is detected, extracted and analyzed as the reference area by means of the object recognition algorithm.

4. The method according to claim 3, characterized in that after creation of at least one of the eye template and the face template the object recognition algorithm is terminated and a comparison algorithm is started, the position of the reference area in the coordinate system of the camera being continuously detected and recorded.

5. The method according to claim 4, characterized in that the shape of the pupil of the eye is nourished by an ellipse, at least one size dimension of the ellipse being detected as a parameter of the pupil and in particular a relative position of a center of the pupil relative to the reference area being determined.

6. The method according to claim 5, characterized in that after creating the face template a calibration process is started in which an orientation of the face and a relative position of the reference area is detected via the face characteristics.

7. The method according to claim 6, characterized in that a reference target is displayed on the display and the absolute and relative position of the eye looking at the reference target is detected.

8. The method according to claim 7, characterized in that after the calibration process the visual stimulus is selected and started in particular from the predefined standard measurement paradigms, at least one of a reaction of the eye, a response latency of the eye, a calculated viewing position of the eye, a pupil size of the eye and a change in the pupil position of the eye being continuously simultaneously detected and recorded in response to certain visual stimuli.

9. The method according to claim 8, characterized in that the pupil of the eye is detected and monitored in ambient light.

10. The method according to claim 9, characterized in that an additional modular lighting unit is activated when unfavorable lighting conditions are present.

11. The method according to claim 8, characterized in that a threshold value for pupil recognition of the camera is adjusted automatically or manually.

12. The method according to claim 8, characterized in that an evaluation is carried out using at least one stored data set and a result of the evaluation is displayed on the display.

13. The method according to claim 12, characterized in that a classification of the determined parameters of the pupil is carried out in particular by means of an externally provided artificial neural network, wherein in particular all newly determined parameters of the eye are entered and in particular taken into account for future classifications.

14. The method of claim 13, characterized in that a tablet PC or smartphone is used to carry out the procedure.

* * * * *